United States Patent [19]
Poto et al.

[11] Patent Number: 5,795,543
[45] Date of Patent: *Aug. 18, 1998

[54] DISPOSABLE ELECTRONIC DIAGNOSTIC INSTRUMENT

[75] Inventors: Edward M. Poto, Somerville; Kenneth R. Strahs, Basking Ridge, both of N.J.; Timothy J. Conner; Francis T. Delahanty, both of Newton, Pa.; Michael Moorman, Princeton; Henry Wieck, Plainsboro, both of N.J.

[73] Assignee: Advanced Care Products, Raritan, N.J.

[*] Notice: The term of this patent shall not extend beyond the expiration date of Pat. No. 5,728,358.

[21] Appl. No.: 897,490

[22] Filed: Jul. 21, 1997

Related U.S. Application Data

[63] Continuation of Ser. No. 339,058, Nov. 14, 1994, abandoned.

[51] Int. Cl.⁶ ............................................. G01N 21/00
[52] U.S. Cl. ................... 422/82.05; 422/55; 422/56; 422/57; 422/58; 422/61; 422/68.1; 436/63; 436/95; 436/169
[58] Field of Search ........................... 422/55–58, 61, 422/68.1, 82.05; 436/46, 63, 95, 166, 169; 435/14, 805, 808, 810

[56] References Cited

U.S. PATENT DOCUMENTS

| | | | |
|---|---|---|---|
| 3,725,658 | 4/1973 | Stanley et al. | 436/117 |
| 3,980,437 | 9/1976 | Kishimoto et al. | 422/55 |
| 4,021,200 | 5/1977 | Farris | 422/82.05 |
| 4,059,405 | 11/1977 | Sodickson et al. | 436/44 |
| 4,160,646 | 7/1979 | Furutani et al. | 436/169 |
| 4,171,909 | 10/1979 | Kramer et al. | 356/73 |
| 4,199,261 | 4/1980 | Tidd et al. | 356/448 |
| 4,558,013 | 12/1985 | Marinkovich et al. | 436/513 |
| 4,689,202 | 8/1987 | Khoja et al. | 422/65 |
| 4,717,545 | 1/1988 | Morris | 422/56 |
| 4,752,447 | 6/1988 | Kimmel et al. | 422/56 |
| 4,820,490 | 4/1989 | Morris | 422/58 |
| 4,867,946 | 9/1989 | Gross et al. | 422/68 |
| 4,949,400 | 8/1990 | Leveen et al. | 356/420 |
| 4,952,373 | 8/1990 | Sugarman et al. | 422/99 |
| 4,985,205 | 1/1991 | Fritsche et al. | 422/56 |
| 5,037,614 | 8/1991 | Makita et al. | 422/68.1 |
| 5,047,351 | 9/1991 | Makiuchi et al. | 436/169 |
| 5,053,197 | 10/1991 | Bowen | 422/58 |
| 5,059,394 | 10/1991 | Phillips et al. | 422/68.1 |
| 5,096,670 | 3/1992 | Harris et al. | 422/65 |
| 5,104,619 | 4/1992 | de Castro et al. | 422/56 |
| 5,114,350 | 5/1992 | Hewett | 435/288 |
| 5,120,507 | 6/1992 | Sano et al. | 422/82.05 |
| 5,147,609 | 9/1992 | Grenner | 422/58 |
| 5,167,922 | 12/1992 | Long | 422/58 |
| 5,173,433 | 12/1992 | Bachand | 436/169 |
| 5,179,005 | 1/1993 | Phillips | 435/14 |
| 5,179,288 | 1/1993 | Miffitt et al. | 250/564 |
| 5,281,395 | 1/1994 | Markart et al. | 422/82.05 |
| 5,316,727 | 5/1994 | Suzuki et al. | 422/68.1 |
| 5,424,035 | 6/1995 | Hones et al. | 422/55 |

FOREIGN PATENT DOCUMENTS

0535485  9/1992  European Pat. Off. .

Primary Examiner—Harold Y. Pyon
Attorney, Agent, or Firm—Paul A. Coletti

[57] ABSTRACT

The invention relates to a disposable electronic diagnostic instrument designed for use in an Over-the-Counter (OTC) cholesterol test kit for measuring cholesterol levels of blood. The instrument is designed and calibrated specifically for use with diagnostic test strips supplied with the OTC cholesterol test kit.

31 Claims, 9 Drawing Sheets

DISPOSABLE ELECTRONIC DIAGNOSTIC INSTRUMENT

This is a continuation of application Ser. No. 08/339,058, filed Nov. 14, 1994, now abandoned.

BACKGROUND OF THE INVENTION

1. Field of the Invention

The present invention relates generally to a disposable electronic diagnostic instrument, and more particularly pertains to a disposable electronic diagnostic instrument designed for use in an Over-the-Counter (OTC) cholesterol test kit for measuring cholesterol levels of blood. The diagnostic instrument is designed and calibrated specifically for use with diagnostic test strips supplied with the OTC cholesterol test kit for measuring and displaying the cholesterol level of a tested whole blood sample.

In greater detail, the subject invention relates to a disposable electronic diagnostic instrument supplied as part of an Over-the-Counter (OTC) cholesterol test kit for measuring blood cholesterol levels. The OTC cholesterol test kit consists of the disposable electronic diagnostic instrument, chemistry test strips to which a whole blood sample is applied, and an instructional leaflet. The OTC cholesterol test kit can optionally include lancet devices, antiseptic alcohol swabs, and adhesive bandages. The OTC cholesterol test kit facilitates accurate measurements of blood cholesterol levels.

One major long term health concern today is the level of cholesterol in a person's blood. It is well known that persons having high levels of blood cholesterol are more susceptible to various heart and circulatory ailments than those having lower blood cholesterol levels. Because blood cholesterol can be managed by a person through diet or medication, it is important for a person concerned about cholesterol level to be able to easily, frequently and accurately measure the concentration of cholesterol in blood in order to be able to take appropriate corrective actions to control blood cholesterol level. Blood cholesterol level is one example of a bodily constituent which is capable of being controlled by individual actions through diet, exercise and the like. It would be highly desirable if an individual could make easy, frequent and accurate measurements of blood cholesterol level.

2. Discussion of the Prior Art

Instruments capable of electronically detecting the colorimetric response of a test strip are commercially available, such as OneTouch ™ available from Lifescan Inc., the Tracer™ II, Accu-Chek® II™, Accu-Chek® Easy™, Accu-Chek® II Freedom™, and the Reflotron® from Boehringer Mannheim Corporation, Clinitek® 1100 System and Glucometer®, available from Ames Division of Miles Laboratories, Rapidimat® II/T available from Behring Diagnostics Inc., Companion™ 2 available from MediSense, Inc., and the Answer™ product available from Wampole Laboratories. Other suitable instruments are similar to those described in U.S. Pat. No. 4,935,346.

SUMMARY OF THE INVENTION

The present invention provides:

A disposable diagnostic instrument calibrated for use with a test strip to which blood is applied, comprising:
  a. an instrument housing having keying guides defining a location at which said strip is placed, and defining a test reading aperture on said strip on which one or more drops of blood to be tested are inoculated, said test reading aperture defining a test area;
  b. a light source positioned to emit radiation of desired wavelengths towards said test area and a photodetector positioned to detect radiation reflected by said test area;
  c. a display mounted on said instrument housing for displaying instrumental prompt icons and cholesterol level readings;
  d. a first control circuit, said first control circuit performing self-diagnostic testing of said instrument;
  e. a second control circuit, said second control circuit controlling the operation of said light source, analyzing the output signal of said photodetector, and controlling the operation of said display.

The disposable electronic diagnostic instrument of the present invention is calibrated to a specific test strip lot and has keying guides defining a location at which a test strip is placed thereby conferring to an Over-the-Counter consumer an accurate and easy instrument for operation. Accordingly, the present invention provides a disposable electronic diagnostic instrument designed for use in an Over-the-Counter (OTC) cholesterol test kit for measuring cholesterol levels of blood. The diagnostic instrument is designed and calibrated specifically for use with diagnostic test strips supplied with the OTC cholesterol test kit, for measuring and displaying the cholesterol level of a tested whole blood sample. The OTC cholesterol test kit consists of the disposable electronic diagnostic instrument, chemistry test strips to which a whole blood sample is applied, and an instructional leaflet. The OTC cholesterol test kit can optionally include lancet devices, antiseptic alcohol swabs, and adhesive bandages. The OTC cholesterol test kit facilitates accurate measurements of blood cholesterol levels.

In accordance with the teachings herein, the present invention provides a disposable electronic diagnostic instrument for operation with a chemical test strip to which blood is applied for measuring the cholesterol level thereof. The instrument housing has keying guides defining a location at which a chemical test strip is placed, and defines a test reading aperture located adjacent to a test spot on the chemical test strip, on which one or more drops of blood to be tested are inoculated. Beneath the test reading aperture, a light source is positioned to emit radiation towards the test spot, and a photodetector is positioned to detect radiation reflected by the test spot. A display is mounted on the instrument housing for displaying instructional prompt icons and cholesterol level readings. A control circuit controls the operation of the instrument, including the operation of the light source, analyzing the output signal of the photodetector, and controlling the operation of the display.

In greater detail, the reflectance characteristics of the test strip have been previously measured, and the measured reflectance characteristics of the test strip are stored in a memory of the control circuit. Measured reflectance characteristics are defined as the reflectance of unreacted dry strip, the percent reflectance having a range of about 65 to 100 percent. The light source comprises a light emitting diode, and the detector comprises a silicon photodiode. The test area of the instrument comprises a planar surface of a circuit board, and the light emitting diode is mounted with its longitudinal light emitting axis substantially perpendicular to the planar surface. The photodiode is mounted spaced from the light emitting diode with its longitudinal light detecting axis also substantially perpendicular to the planar surface, and a flare screen is positioned between the light emitting diode and the photodetector. An optical filter, having bandpass characteristics matching the emission wavelengths of the light emitting diode, is mounted over the light emitting diode and photodetector. The optical filter defines the bandpass characteristics (narrow wavelength band) which is required to read color development of the test strip and reduces interference caused by the external light on detector.

Calibration threshold levels are stored in the memory of the control circuit for cholesterol threshold levels of 100 mg/dL, 200 mg/dL, and 240 mg/dL. The control circuit is implemented in an Application Specific Integrated Circuit (ASIC), and the display is a liquid crystal display. The keying guides of the instrument include at least one lateral edge guide for engaging a lateral edge of the test strip, and an angled fore guide for engaging an angled fore edge of the test strip. The angled fore guide is positioned off-center with respect to the chemical test strip, such that the angled fore edge of the chemical test strip can properly engage the angled fore guide only when the chemical test strip is properly positioned in the instrument housing, not in a reversed or upside down position. A sensor switch is located adjacent to the fore guide for activating the control circuit in response to a test strip being placed in the electronic diagnostic instrument. After a test strip is inserted in the electronic diagnostic instrument, the control circuit initiates a test reading to determine if the inserted test strip has optical reflectance characteristics within an acceptable range. The control circuit causes the liquid crystal display to display prompt icons during usage of the instrument, including an add blood icon, a timer icon, and an error icon. The control circuit causes the liquid crystal display to display one of three cholesterol level readings, an under 200 reading, a 200 to 240 reading, and an over 240 reading. These levels correspond with established risk factors for coronary heart disease.

BRIEF DESCRIPTION OF THE DRAWINGS

The disposable electronic diagnostic instrument of the present invention may be more readily understood by one skilled in the art with reference to the following detailed description taken in conjunction with the accompanying drawings wherein like elements are designated by identical reference numerals throughout the several views, and in which.

DETAILED DESCRIPTION OF THE DRAWINGS

Figure 1:
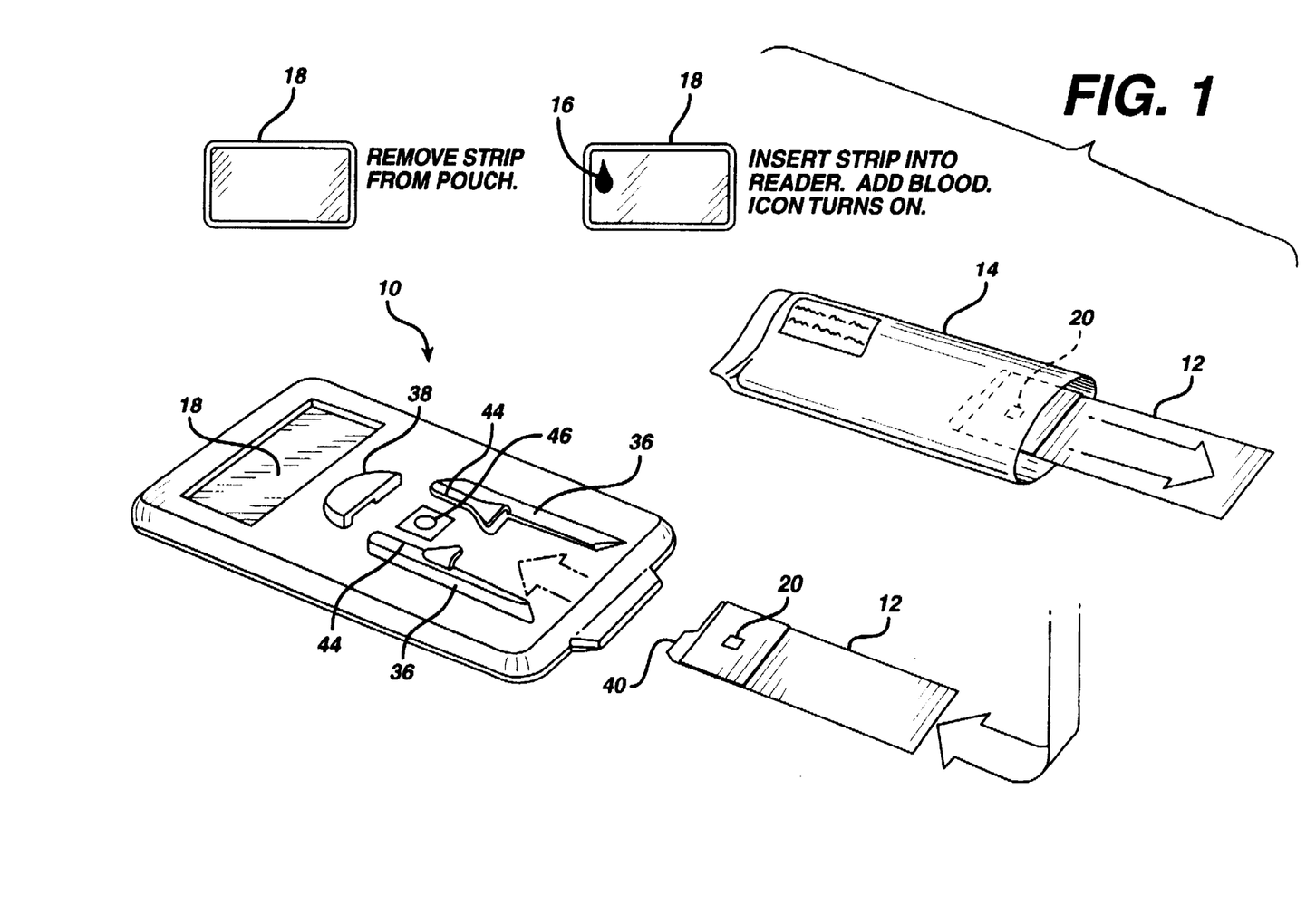
FIG. 1 is a schematic view of an exemplary test instrument pursuant to the teachings of the present invention, illustrating the pre-test strips for the exemplary test instrument, an exemplary test strip being removed from a protective package and being placed in the instrument, and a prompt icon displayed on the test instrument LCD display upon insertion of the test strip.

Referring to the drawings in detail, FIG. 1 is a schematic view of an exemplary disposable electronic diagnostic test instrument 10 constructed pursuant to the teachings of the present invention. The present invention relates to an Over the Counter (OTC) product for measuring blood cholesterol levels, which is a kit consisting of the disposable electronic test instrument 10, chemistry test strips 12 to which whole blood is applied, and an instructional leaflet, and can optionally include lancet devices, antiseptic swabs, and adhesive bandages.

The electronic device for the OTC cholesterol test is disposable, and one kit can comprise 1 diagnostic test instrument 10 and a defined number of test strips 12. In a preferred embodiment the kit comprises 3 of such test strips. After using the strips, the diagnostic test instrument 10 is discarded. The kit and strips together are batch specific, such that a user cannot use strips 12 from one batch with a diagnostic test instrument 10 from a different batch. The diagnostic test instrument 10 is activated by a strip insertion, and automatically performs a self-diagnostic test (first control circuit) every time it is activated. The user is prompted by icons throughout usage, and the final result is qualitative but is given in a quantitative format.

FIG. 1 also illustrates the pre-test steps for the exemplary test instrument 10, in which a test strip 12 is removed from a protective package 14 and is placed in the instrument 10. A prompt icon 16 (♦) is displayed on the test instrument LCD display 18 upon successful insertion of a test strip 12, to prompt the user to add a drop of blood to a test spot area 20 on the test strip 12.

Figure 2:
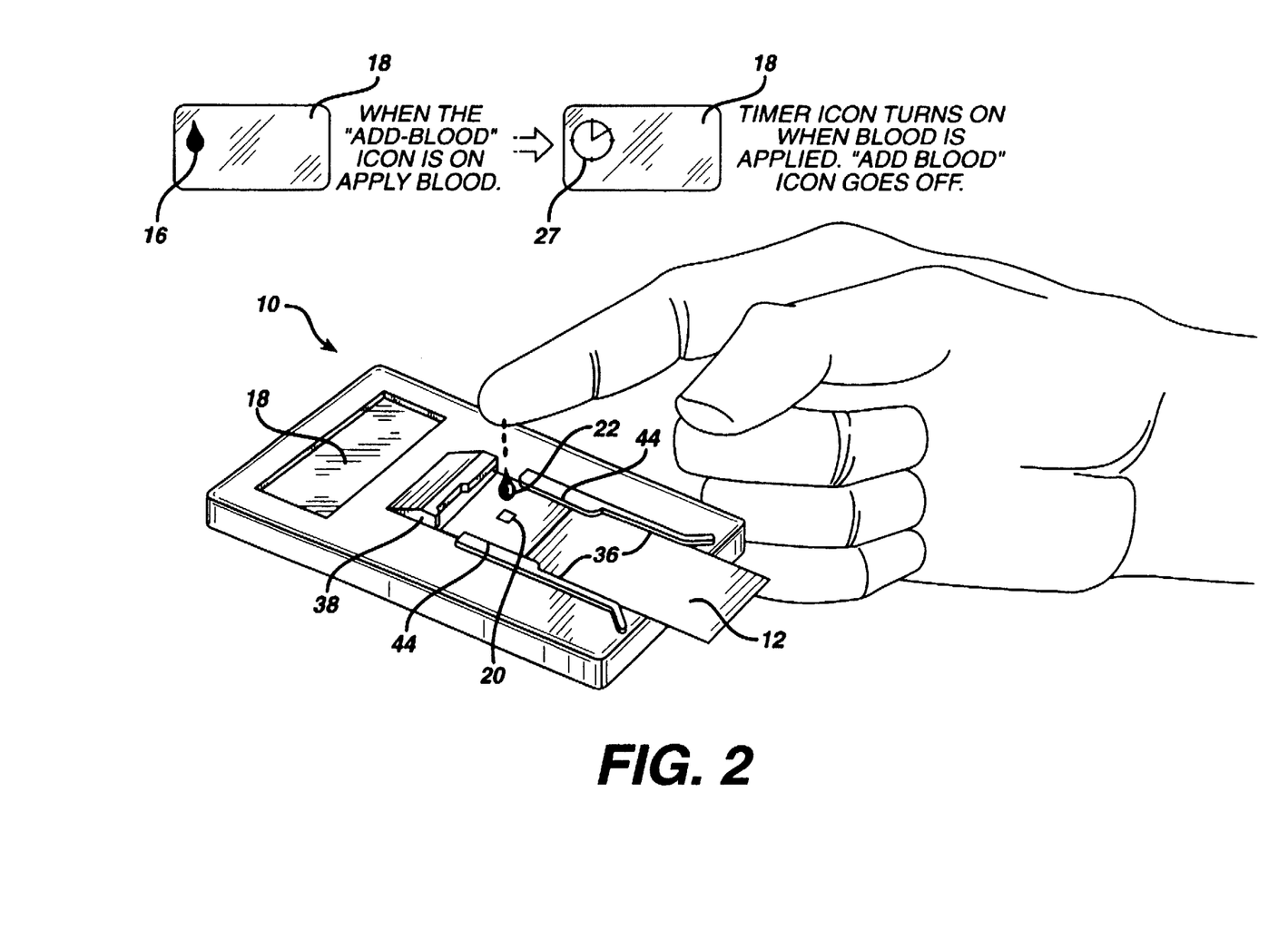
FIG. 2 illustrates the inoculation of a drop of blood to the test strip in the test instrument, and shows the prompt and instructional icons displayed on the test instrument LCD display during those steps.

FIG. 2 illustrates the addition of a drop of blood 22 to a test strip positioned in the disposable electronic diagnostic test instrument, and shows the prompt and instructional icons 16 and 24, FIG. 2, displayed on the test instrument LCD display 18 during these steps.

Figure 3:
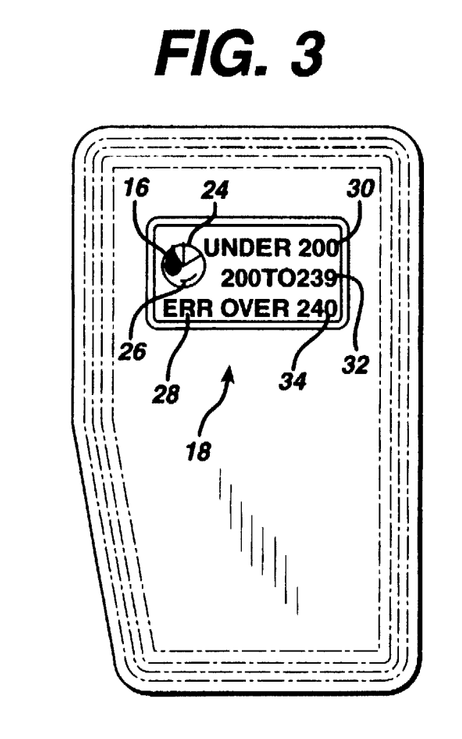
FIG. 3 illustrates the test instrument LCD display, with all possible prompt and instructional icons and all possible cholesterol readings being simultaneously displayed thereon.

FIG. 3 illustrates the test instrument LCD display 18 with all prompt and instructional icons and all possible cholesterol readings being simultaneously displayed thereon, including:

a. a Clock icon 24 (○) on the meter's display which indicates that the meter is operating and not waiting for a user operation;

b. an Add Blood icon 16 (♦) on the meter's display which prompts the user to add a drop of blood onto the test strip that has been fully inserted into the meter;

c. a Check Mark icon 26 (√) on the meter's display which indicates a diagnostic mode of operation. This mode is not used by a consumer but may be used by manufacturers and quality control professionals to check the performance or calibration of the meter;

d. an Error icon 28 (ERR) on the meter's display which indicates an error condition;

e. an Under 200 icon 30;

f. a 200 to 239 icon 32; and g. an Over 240 icon 34.

The LCD displays one of four results as set forth in the following Table 1.

TABLE 1

| Meter Interpretation | Meter Display | Reading |
| --- | --- | --- |
| Error | ERR | Defective Strip |
| Error | ERR | Less than 100 mg/dL |
| Desirable | Under 200 | 100 to 199 mg/dL |
| Borderline | 200 to 239 | 200 to 239 mg/dL |
| High | 240 & Over | 240 mg/dL or more |

Figure 4:
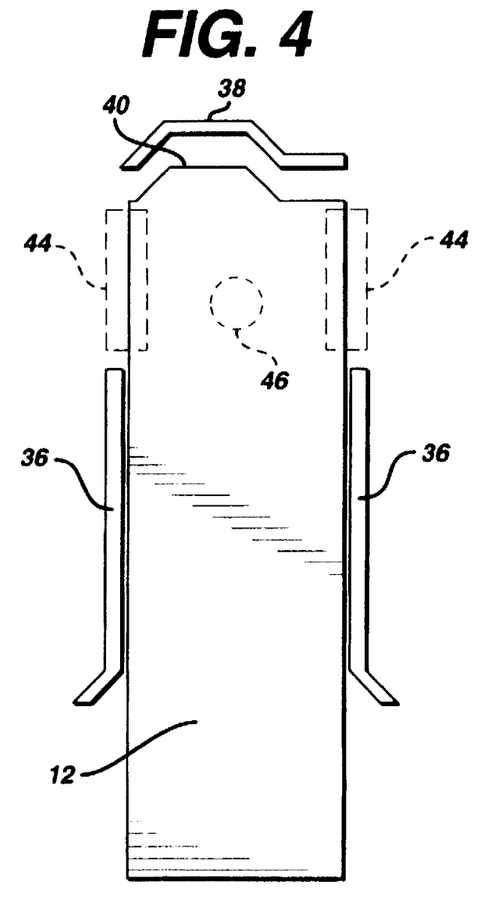
FIG. 4 shows corresponding keying features of the test strip and the test instrument for properly positioning the test strip in the test instrument.

FIG. 4 shows corresponding keying features of the test strip 12 and the test instrument 10, FIG. 1, for properly positioning the test strip in the test instrument. The test strip shape combined with features in the instrument housing provides for self-location of the test strip in a test aperture provided on the instrument housing. The instrument includes positional guides for ensuring that the test strip is properly positioned with respect to the instrument, which include two lateral edge guides 36 for engaging two lateral edges of the test strip 12 and an angled fore guide 38 for engaging a corresponding angled fore edge tab 40 of the test strip, as shown more clearly in FIG. 4. The angled tab 40 is positioned off-center with respect to the chemical test strip, such that the angled tab 40 of the chemical test strip 12 can properly engage the angled fore guide 38 only when the chemical test strip 12 is properly positioned in the instrument housing, not in a reversed or upside down position. A test strip sensor switch 42, FIG. 6, is located adjacent to the fore guide 38 for activating the first control circuit in response to a test strip 12 being placed in the electronic diagnostic instrument 10, FIG. 1.

Figure 6:
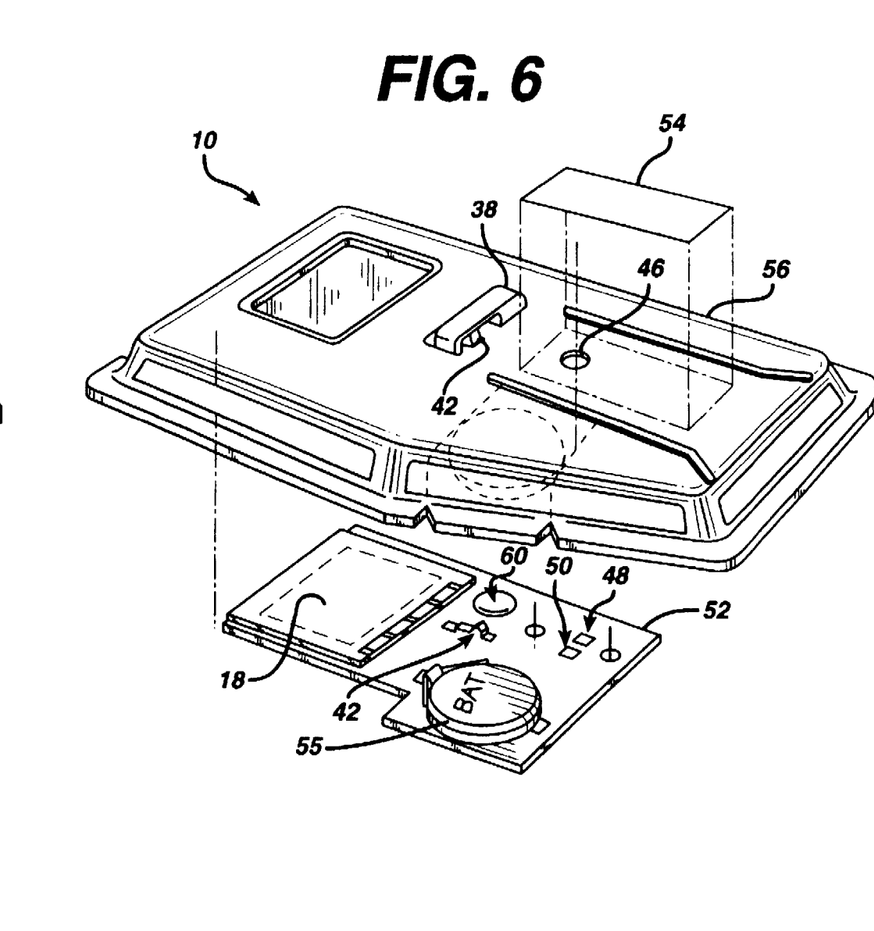
FIG. 6 is an exploded view of the electronic test instrument, showing the electronic circuit board therefor and other features of the test instrument.

The lateral edge guides 38 are supplemented by hold down tabs 44, FIG. 4, for properly positioning the test spot area 20, FIG. 2, on the chemical test strip 12, on which one or more drops of blood to be tested are inoculated, relative to a test reading aperture 46, FIG. 6, in the instrument. The aperture 46 has therebelow a test area in which a light emitting diode 48, FIG. 6, is positioned to emit radiation toward the test spot 20, FIG. 2, and a silicon photodiode 50, FIG. 6, is positioned to detect radiation reflected by the test spot.

Figure 5:
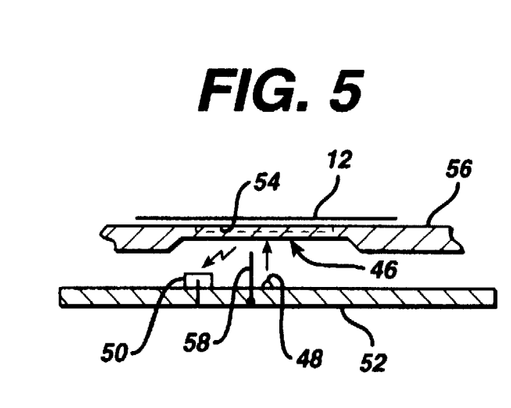
FIG. 5 illustrates the optical detecting arrangement of the test reading area of the instrument, showing the positional relationships of the several components of the optical detecting arrangement.

FIG. 5 illustrates the optical detecting arrangement of the test reading area of the instrument 10, FIG. 6, showing the positional relationships of several components of the optical detecting arrangement. The electronic instrument 10 is designed with a planar sensor geometry in which the LED emitter 48 and the photodiode detector 50 are mounted on a circuit board 52 with their normal axes parallel to the strip surface normal axis. In greater detail, the light emitting diode 48 is mounted with its longitudinal light emitting axis substantially perpendicular to the planar surface, and the photodiode 50 is mounted spaced from the light emitting diode 48 with its longitudinal light detecting axis also positioned substantially perpendicular to the planar surface of the circuit board 52. The LED emitter 48 is well diffused and displaced from the detector to avoid detection of specular reflections.

Some amount of stray room background light will be incident on the detector 50. The amount of background illumination is minimized by the illustrated mechanical design of the instrument and by the use of an optical bandpass filter 54, FIG. 6, having bandpass characteristics matching the desired measured wavelengths of the LED 48, mounted over the LED 48 and the photodetector 50 and beneath the test strip 12. The effect of background illumination is further reduced by sampling the detector signal level with the emitter disabled and subtracting this signal from the intended signal, as explained in greater detail hereinbelow with reference to FIGS. 7 and 8.

Two factors that greatly influence the alignment tolerances of the test strip 12 with respect to the test instrument are the flare and specular contributions, as discussed hereinbelow.

Internal flare is the signal due to reflected light from surfaces other than the test strip 12, and has the effect of reducing the apparent measurement contrast. Internal flare is minimized through careful housing design and by the selection of materials or coatings with low reflectance. Residual internal flare value is measured at the factory and stored in memory.

The sensitivity of the emitter/detector system to specularity impacts upon the apparent contrast of the measurement and might introduce measurement errors due to the variability in the specularity of the test strip 12 (which is largely a function of how much blood is applied thereto), which is minimized through careful design of the geometry of the emitter/detector system.

Accordingly, the geometry of the emitter/detector system is quite important to the accuracy of the measurement. One selected geometry is a 3.75 mm separation between the LED 48 and the photodiode 50 (longitudinal axis to longitudinal axis) and a 2.5 mm separation between the upper surface of the circuit board 52 and the lower surface of the instrument strip receiver housing. Contribution of the specular image affects alignment sensitivity in the y (left-right)and z (up-down) directions, and the LED/photodiode separation (center to center) has been selected to be 3.75 mm to reduce this sensitivity. A flare screen 58 is also placed between the LED and the photodetector 50 to reduce the flare contribution. The flare screen 58 comprises a 1.49 mm tall by 2.8 mm wide flare barrier placed 0.8 mm from the center of the LED 48 to reduce the flare contribution, and also results in a reduction in the alignment sensitivity in the x and y directions in the sensor plane.

FIG. 6 is an exploded view of the electronic test instrument, showing the electronic circuit board 52 and other features of the test instrument. The test instrument has all of the circuitry including the ASIC 60, the optical components, and a power supply battery 55 mounted on a single circuit board 52, which is mounted in an outer housing 56.

The test strips 12 to be used with the disposable electronic diagnostic instrument of the present invention preferably are based upon the use of a dry reagent chemistry. In dry reagent chemistry, the reagent chemicals are stored in a dry state in a single device which also incorporates a reaction chamber as part of the structure. This integration of the different components has the advantage of requiring much less automation or operator intervention. Fluid contained in the sample activates the test chemicals, and the matrix that holds the test chemicals usually undergoes a color change that can be read directly without further processing. The basic chemistry involved in testing blood cholesterol levels is well known. U.S. Pat. No. 3,907,645 (Richmond) discloses a method and kit for assaying cholesterol in a liquid. The disclosed cholesterol assay involves incubating the liquid to be tested with an enzyme preparation which is derived from Norcardia species. The enzyme preparation oxidizes any cholesterol present in the liquid into cholestenone and hydrogen peroxide. The amount of cholesterol is determined by measuring the amount of hydrogen peroxide produced.

The chemistry test strips used with the disposable electronic diagnostics instrument of the present invention can be of the type disclosed in U.S. patent application Ser. No. 08/115,946, filed Sep. 1, 1993, now abandoned, for a DEVICE AND METHOD FOR CONDUCTING BIOLOGICAL ASSAYS CONTAINING PARTICULATE SCREENING SYSTEM. That patent application discloses a chemical test strip for conducting biological assays which uses a particulate screening system to remove contaminating substances from the biological sample. The particulate screening system comprises a blood separation matrix, a flow control hydrophilic screening matrix, and a reagent matrix with at least one hydrophilic microporous membrane having incorporated therein a calorimetric detection system for an analyte. The device is adapted to detect, and in some cases quantitatively or semi-quantitatively measure, an analyte present in a biological fluid so that a color change is observed when the fluid is brought into contract with the reagent membrane pad containing the detecting system. The system is particularly suitable for glucose or cholesterol detection devices where a small capillary blood sample is preferred and presence of particulate matter in the biological sample, most notably red blood cells, would be a hindrance to the analytical results.

Figure 7:
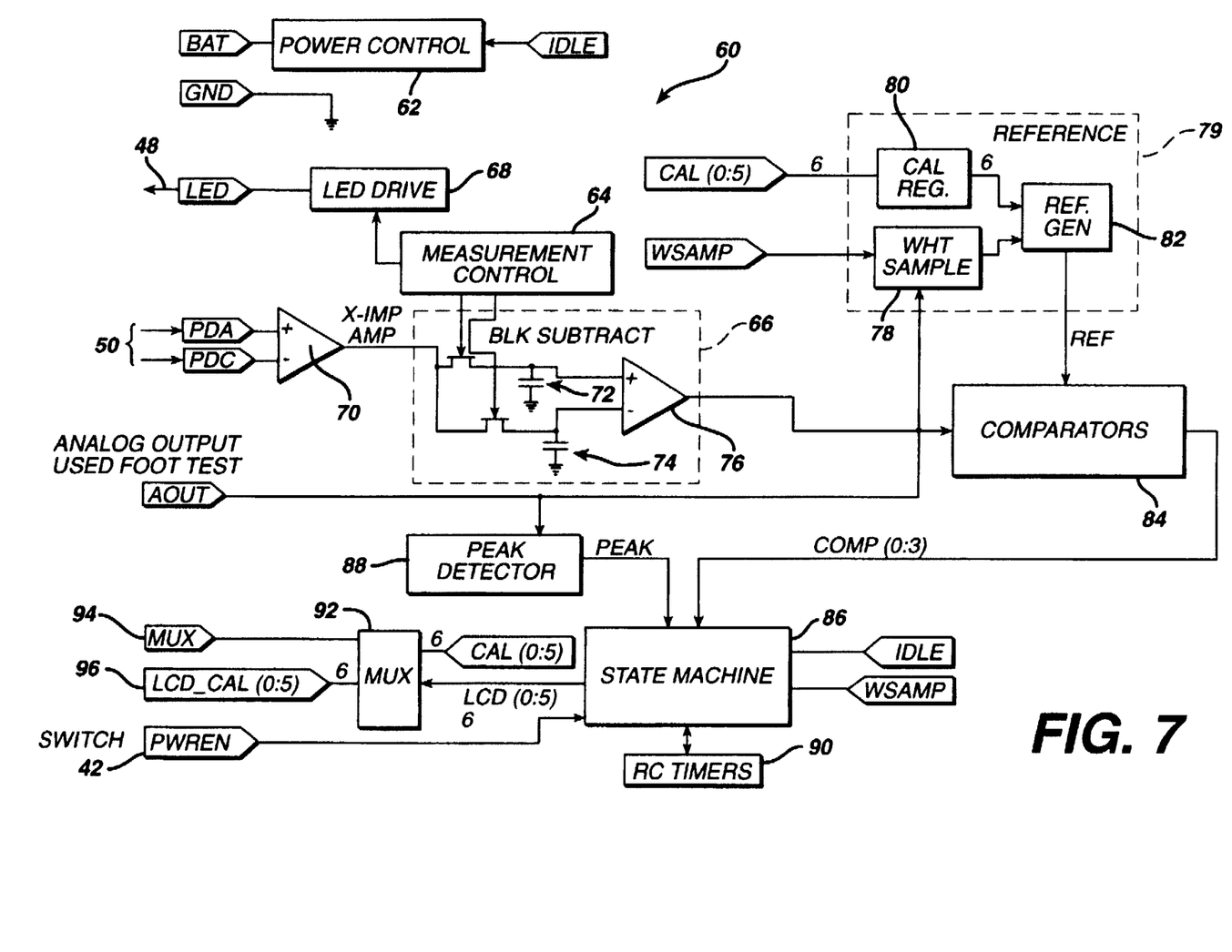
FIG. 7 is an electrical block diagram of the control circuit for the test instrument.
Figure 8:
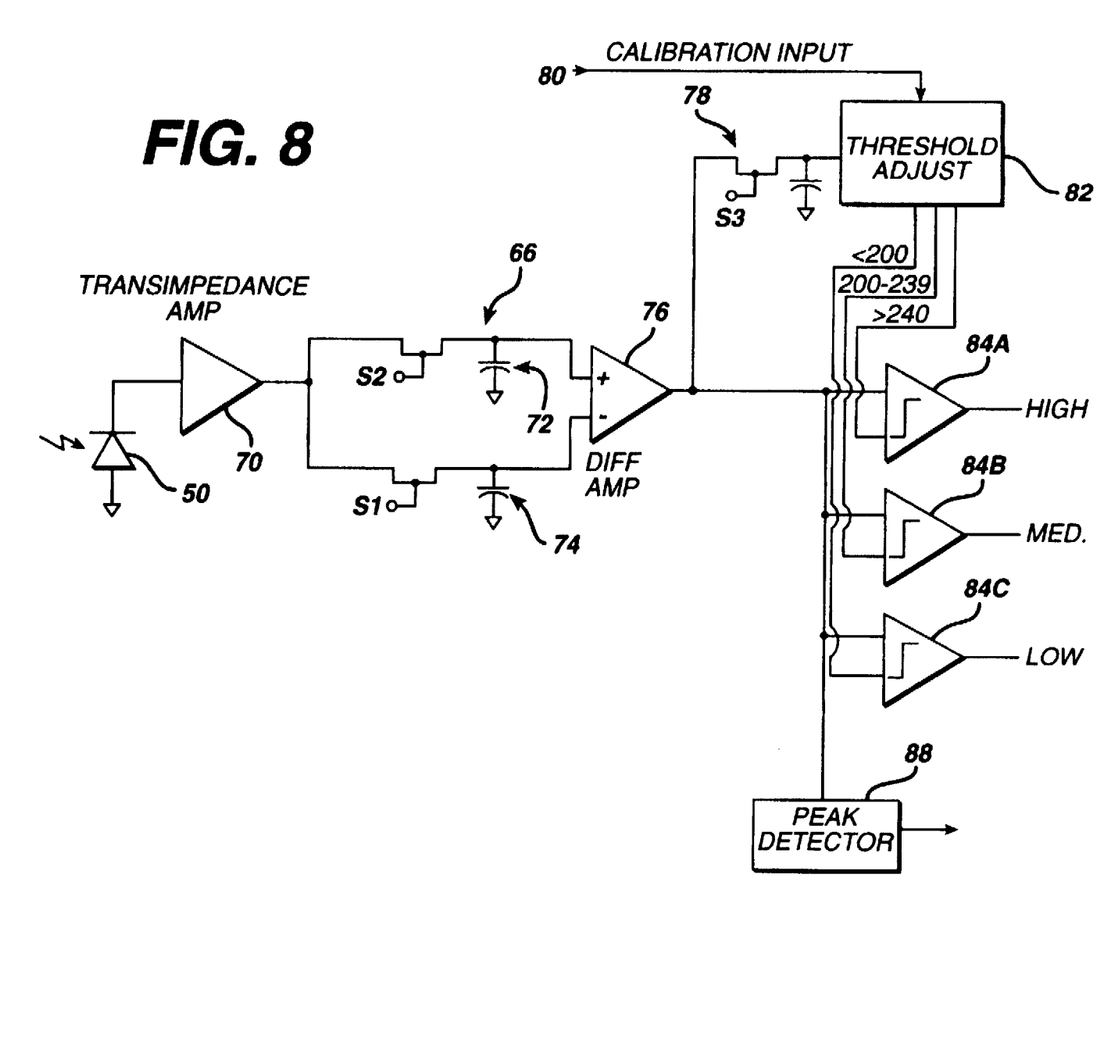
FIG. 8 illustrates further details of the comparators and threshold adjustments of the control circuit for the test instrument.

FIG. 7 is an electrical block diagram of the electronic control circuit for the test instrument, while FIG. 8 illustrates in further detail the comparators and threshold adjustments of the electronic control circuit. The electronic cholesterol disposable test instrument is provided with an Application-Specific Integrated Circuit (ASIC) 60, which is a custom designed integrated circuit that controls the meter. The electronic system controls the operation of the instrument and prompts the user through the proper sequence of operational steps. The custom mixed-signal ASIC 60 includes all of the electronics for the first and the second control circuits to:

control the Power-On Self-Test (POST), calibration and cholesterol test sequencing;

drive the display 18, FIG. 6;

drive the sensor 50/emitter 48;

process the sensor 50 detector signal; and calibrate the unit.

The sensor system is controlled by the ASIC 60, and the two primary components thereof, the light-emitting diode 48 and the photodiode detector 50, and bare dice epoxy-mounted to the circuit board 52, and connections to the ASIC 60 are provided by traces on the circuit board.

The liquid crystal display 18, FIG. 6, is controlled by the ASIC 60 using a direct (non-multiplexed) drive mode to reduce complexity. The LCD 18 clearly displays all user prompts, status conditions, and qualitative test results in a relatively small viewing area.

FIG. 7 is a block diagram of the major components of the control circuits as they are implemented in the ASIC 60. A Power Control circuit 62 shuts off power to the majority of the circuitry when the device is in an IDLE mode. A Measurement Control circuit 64 generates timing signals used to pulse the LED 48 and to control a Black Subtraction circuit 66, explained in greater detail hereinbelow. The timing signals comprise three synchronous signals having defined phase relationships and a period of approximately 1 msec. An LED Drive circuit 68 provides the LED 48 with approximately 5 mA current pulses. A transimpedance amplifier 70 amplifies and buffers the signals from the photodiode 50, and is a high gain, low noise circuit. The photodiode 50 can be similar to Photonic Detector's part PDB-V101, operated in a photovoltaic mode.

The Black Subtract circuit 66 samples the photodiode output when the LED 48 is off and when it is on. These two sample signals are low-pass filtered at 72, 74, and are subtracted using a differential amplifier 76. The resultant signal represents a signal normalized to eliminate the effects of background radiation. In a Reference Circuit 79, a White Sample circuit 78 samples and holds the output of the Black Subtract circuit 66 prior to a user's addition of a blood sample to the test strip 12, FIG. 2. The sampled value, along with the output of a calibration register 80, are used by a reference generator 82 to generate a reference voltage which is divided and supplied as three different threshold voltage to three comparators at 84. The three comparators at 84 compare the output of the Black Subtract circuit 66 with voltages divided from the reference voltage. The outputs of the comparators are supplied as inputs to a State Machine 86. A Peak Detector circuit 88 senses when the slope of the output of the Black Subtract circuit 66 has reversed. The Peak Detector 88 output is supplied to the State Machine 86, which performs the logic and control functions as described herein. Two one-shot timers at 90 generate timing intervals for use by the State Machine, at 5±1 minute and 15±5 minute intervals.

A multiplexer 92, under control of an MUX input signal at 94, controls the routing of the LCD_CAL[0:5] I/O lines at 96. During factory calibration of the instrument, the MUX 92 is driven active and calibration data on the test strips is supplied on the LCD_CAL[0:5] lines 96 and directed to the Reference circuit 79 where these values are programmed into and stored in an OTP register 80. Each instrument is calibrated for a specific chemistry lot prior to final packaging. This calibration function is provided by the ASIC, and includes a serial communications link to the programming device. Calibration data is retained in a static memory within the ASIC. During normal operation, the State Machine outputs LCD[0:5] at 96 statically drive the custom, six-segment LCD 18.

The various inputs and outputs illustrated on the left side of FIG. 7 have the following meanings.

| Name | Description |
| --- | --- |
| BAT | 3V Lithium battery input |
| GND | Ground connection |
| LED | LED Drive Output |
| PDA | Connection to Photodiode Anode |
| PDC | Connection to Photodiode Cathode |
| AOUT | Analog Output used for Test |
| LCD_CAL [0:5] | Multiplexed LCD Drive Outputs/Inputs for Programming Calibration Values |
| MUX | Mux select for LCD_CAL [0:5] |
| PWREN | Input from Power-On Contact |

FIG. 8 illustrates in further detail the signal processing in which an output signal from the photodiode detector 50 is amplified by transimpedance amplifier 70. The Black Subtract circuit 66 samples (controlled by sample timing signals S1, S2 from measurement control circuit 64, FIG. 7) the amplified photodiode output when the LED 48, FIG. 7, is off and when it is on. These two sample signals are low-pass filtered at 72, 74 and are subtracted by the differential amplifier 76. The White Sample circuit 78 (controlled by timing signal S3 from measurement control circuit 64, FIG.

7) samples and holds the output of the Black Subtract circuit 66 prior to a user's addition of a blood sample to the test strip 12. FIG. 1. The sampled value, along with a calibration input from calibration register 80, is used by reference generator 82 to generate a reference voltage which is then voltage divided (as by resistor voltage dividers) to derive three reference threshold voltages representative of >240, 200–239, <200, which are supplied to three comparators 84A, 84B and 84C. The three comparators compare the output of the Black Subtract circuit 66 with the voltages divided from the reference voltage. A Peak Detector circuit 88 senses when the slope of the output of the Black Subtract circuit 66 has reversed. The outputs of the comparators 84 and the output of the Peak Detector 88 are supplied to the State Machine 86, which performs the logic and control functions as described herein.

Figure 9:
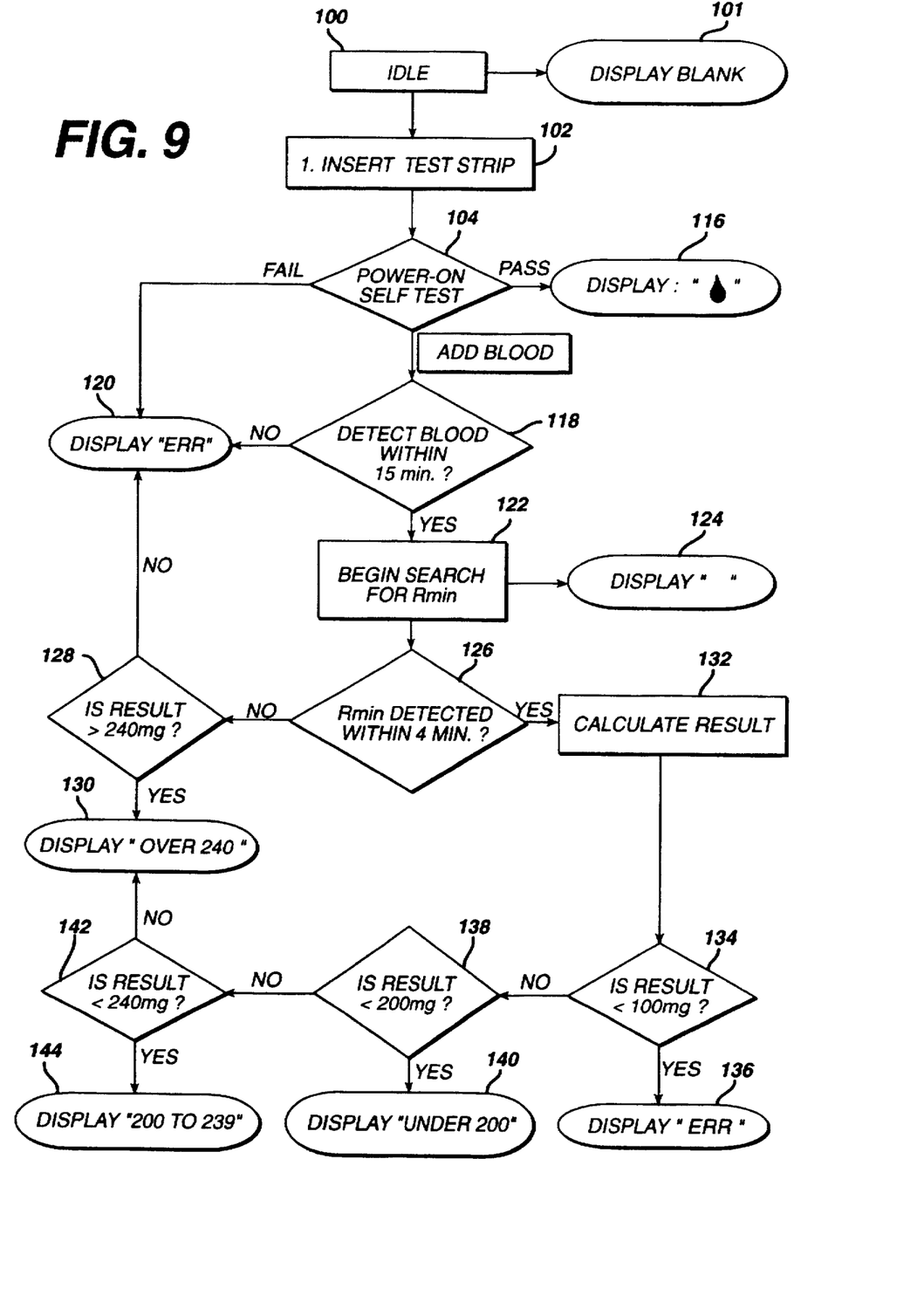
FIG. 9 is an operational flow diagram of the electronic test instrument.

FIG. 9 is an operational flow diagram of the electronic test instrument. The power circuit 62, FIG. 7, normally maintains the instrument in an idle mode 100, during which power consumption is minimal and the display is blank, block 101. The insertion of a test strip 12, block 102, activates the instrument by the strip sensor switch 42, FIG. 6. The power control circuit 62, FIG. 7, automatically turns the instrument off when a test is completed or when the test strip is removed in order to reduce power consumption.

Full insertion of an undeveloped test strip initiates a first control circuit with the Power-On Self-Test (POST) sequence 104, which is a diagnostic routine automatically performed when a strip is inserted to verify proper sensor operation. The first control circuit is illustrated in further detail in FIG. 10. If the POST is passed, a flashing add blood prompt icon 16, FIG. 2, appears on the display, block 116, FIG. 9. If the POST is failed, one of two possible error displays will result.

Figure 10:
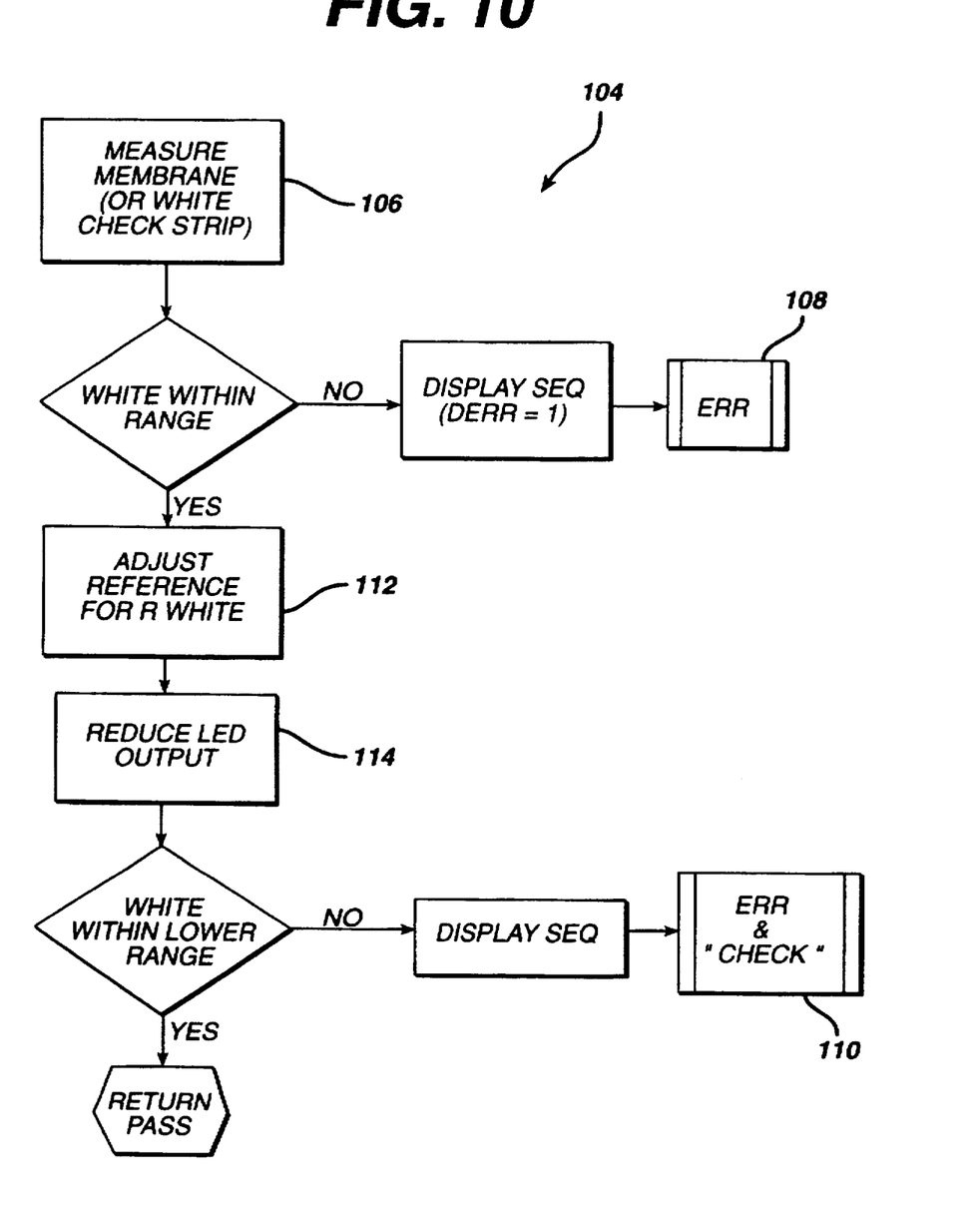
FIG. 10 is a logic flow diagram illustrating a power-on self-test of the electronic test instrument.

1. Referring to FIG. 10, an ERR icon at 108 indicates that the underdeveloped test strip did not exceed the Rw threshold.
2. An ERR and √ icon at 110 indicates that the Instrument Verification test has failed.

When the instrument is turned on, the POST sequence illustrated in FIG. 10 checks the reflectance of the test strip at 106. If there is an optical or electronic failure in the instrument, it does not accept the test strip and reports an error without further testing. The instrument also rejects all test strips that are too dark. Thus phony strips, used strips, strips that were exposed to humidity for long periods of time are rejected. After accepting the test strip, the reference is adjusted for Rw at 112, and the instrument next performs an internal "electronic check strip" procedure at 114 in which the test strip is illuminated with less energy, and the instrument verifies that an appropriate signal is obtained from the detector. If not, an ERR and √ are displayed at 110.

Referring back to FIG. 9, second control circuit takes the control of the instrument when the POST sequence from the first control circuit passed successfully. At this point an add blood icon 16, FIG. 1, is displayed at 116. If no action occurs within 15 minutes, block 118, the instrument displays ERR at 120. When blood has been detected, the instrument proceeds to the Measurement sequence by searching for a detected $R_{MIN}$ at 122. At the beginning of the Measurement sequence, the flashing ♦ is disabled and ⊙ is displayed at 124.

When blood is detected, the instrument has 4 minutes to detect $R_{MIN}$ block 126. If $R_{MIN}$ is not detected within 4 minutes, the instrument checks if the measured result is greater than the 240 threshold, block 128, and if not, ERR is displayed, block 120. This means that a maximum color was not detected within 4 minutes, but the result obtained at 4 minutes indicates less than 240 mg/dl cholesterol. In this manner, the instrument is able to reject strips that have lost so much activity (age or unusual exposure) that they are unable to achieve the end if reaction within 4 minutes. If the reflectance is greater than the 240 mg/dL threshold, the instrument displays the 240 & Over result at 130.

If the peak detector circuit detects $R_{MIN}$ the result is determined by comparing the measurement against the 100 mg/dL and 200 mg/dL thresholds, block 132, and one of the following results is displayed:

a. If the measurement is less than the 100 mg/dL threshold, block 134, ERR is displayed at 136. When an insufficient amount of blood is added to the strip and a part of the reading surface remains dry, the meter will detect less than 100 mg/dl cholesterol and report the error message;

b. If the measurement is greater than the 100 mg/dL threshold and less then the 200 mg/dL threshold, block 138, Under 200 is displayed at 140; and c. If the measurement is greater than the 200 but less than the 240 mg/dL threshold, block 142, 220 to 239 is displayed at 144;

d. If the measurement is greater than the 240 mg/dL threshold, Over 240 is displayed at 130.

When the result of the test is displayed, the displayed result will blink for 5 minutes. During that time, the user will be able to remove the test strip from the meter for an inspection. The instructions illustrate examples of acceptable and unacceptable strips, providing the user with the ability to accept or reject the result.

If during the above procedure the strip is removed and the instrument senses that the Power Enable switch is not activated, the meter returns to an IDLE state controlled by the first control circuit.

Figure 11:
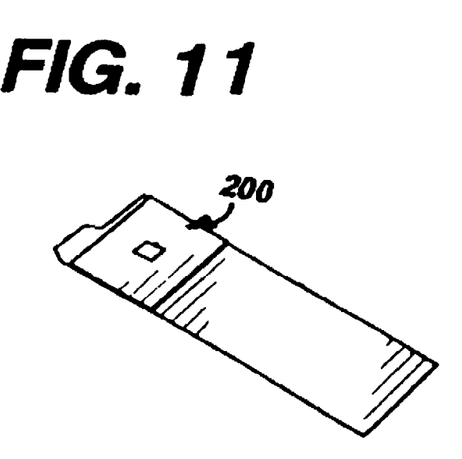
FIG. 11 is a perspective view of a first and second strip as described herein.

The electronic cholesterol disposable test instrument can also be provided with a Static Diagnostic Test (SDT), which is a diagnostic routine that involves placing a special diagnostic strip in the unit. The Static Diagnostic Test (SDT) is initiated by the user performing the following sequence:

1. The white check strip is fully inserted while the instrument is in the idle mode;
2. When the flashing ♦ appears on the display, the white check strip is removed and the SDT check strip 200 (which does not activate the Power Enable switch) is inserted FIG. 11. At this time, all icons are disabled.

During the SDT, the instrument tests for the first three possible events;

1. If operator inserts a normal test strip, the Power Enable switch is activated, in which case the first control circuit is initiated with the POST test;
2. If operator inserts an SDT check strip, the result is displayed provided that the Power Enable switch is not activated;
3. If no action occurs within 10 seconds, the instrument returns to the idle state and all displayed icons are disabled.

When any result or graphical icon is displayed, the icon is flashed until one of two events occurs:

1. The user removes and inserts a strip, in which case the instrument initiates the POST sequence;
2. If no action occurs within 4 minutes, the icon is displayed steadily and the instrument waits for one of two events to occur:
   a. If the user removes and inserts a strip, the POST sequence is initiated;

b. If no action occurs within 15 minutes, the instrument returns to the idle mode and all displayed icons are disabled.

The instrument is easy to hold (approximately credit card length and width), allows right- or left-handed use, and the display provides an unmistakable result, easily read in average ambient lighting.

While several embodiments and variations of the present invention for a disposable electronic diagnostic instrument are described in detail herein, it should be apparent that the disclosure and teachings of the present invention will suggest many alternative designs to those skilled in the art.

What is claimed is:

1. A disposable diagnostic instrument calibrated for use with a test strip to which a blood sample is applied, comprising:
   a. an instrument housing having keying guides defining a location as which said strip is placed, and defining a test reading aperture on said strip on which one or more drops of blood to be tested are inoculated, said test reading aperture defining a test area;
   b. a sensor switch located adjacent said keying guide and contacted by the strip in response to the strip being inserted into the guide, and a control circuit, the switch connected to the control circuit for activation of the instrument by providing power to the instrument in order to operate the instrument
   c. a light source positioned to emit radiation of desired wavelengths towards said test area and a photodetector positioned to detect radiation reflected by said test areas said light source and photodetector capable of analyzing said blood sample at said desired wavelengths to determine the amount of cholesterol in said blood sample;
   d. a display mounted on said instrument housing for displaying instrumental prompt icons and cholesterol level readings;
   e. a first control circuit, said first control circuit capable of performing self-diagnostic testing of said instrument to determine the capability of said photodetector to read said light source within a desired range;
   f. a second control circuit, said second control circuit controlling the operation of said light source, analyzing the output signal of said photodetector, and controlling the operation of said display;
   wherein said instrument measures the change in reflectance of said strip in response to a test solution being applied to said strip, and wherein said keying guides include at least one lateral edge guide for engaging a lateral edge of strip and an angled fore guide for engaging an angled fore edge of said strip.

2. The diagnostic instrument according to claim 1, wherein said second control circuit is implemented in an application specific integrated circuit.

3. The diagnostic instrument according to claim 1, wherein said display comprises a liquid crystal display.

4. The diagnostic instrument according to claim 1, wherein said keying guides include at least one lateral edge guide for engaging a lateral edge of said strip and an angled fore guide for engaging an angled fore edge of said strip, said angled fore guide being positioned off-center with respect to said strip, such that said angled fore guide only when said strip is properly positioned in said instrument housing.

5. The diagnostic instrument according to claim 1, wherein said second control circuit causes said liquid crystal display to exhibit a cholesterol level reading.

6. The diagnostic instrument according to claim 1 wherein said second control circuit comprises a memory, and said strip comprises measured reflectance levels, wherein said measured reflectance levels are stored in said memory of said second control circuit.

7. The diagnostic instrument according to claim 6 wherein said second control circuit memory comprises an internal flare value.

8. The diagnostic instrument according to claim 1, wherein said light source comprises a planar surface, said light source is mounted with its longitudinal light emitting axis substantially perpendicular to said planar surface, and said photodetector is mounted spaced from said light emitting diode with its longitudinal light detecting axis substantially perpendicular to said planar surface.

9. The diagnostic instrument according to claim 8, wherein said light source comprises a light emitting diode, and said photodetector comprises a silicon photodiode.

10. The diagnostic instrument according to claim 8, wherein a flare screen extending substantially perpendicular to said planar surface is positioned between said light emitting diode and said photodetector.

11. The diagnostic instrument according to claim 8, including an optical bandpass filter, having bandpass wavelengths matching said desired wavelengths said optical filter mounted over said light source and said photodetector.

12. The diagnostic instrument according to claim 1, wherein insertion of said strip into said instrument activates said first and second control circuits.

13. The diagnostic instrument according to claim 12, wherein said activation of said first control circuit determines optical reflectance levels of said strip.

14. The diagnostic instrument according to claim 1, wherein said second control circuit contains a memory, said memory storing calibration threshold levels.

15. The diagnostic instrument according to claim 14 wherein said calibration threshold levels comprise cholesterol threshold levels of about 100 mg/dl, 200 mg/dl and 240 mg/dl.

16. The diagnostic instrument according to claim 1, wherein insertion of said strip into said instrument activates said first control circuit wherein optical reflectance levels of said strip are determined.

17. The diagnostic instrument according to claim 16, wherein a sensor switch is located adjacent said fore guide for activating said first control circuit in response to said strip being inserted into said instrument.

18. The diagnostic instrument according to claim 17, wherein after said strip is inserted into said instrument, said first control circuit reduces power output of said light source and takes a reading as an internal check of the performance of said circuits.

19. The diagnostic instrument according to claim 1, wherein said second control circuit causes said liquid crystal display to exhibit prompt icons during usage of said instrument, said icons comprising an add blood icon, a timer icon and an error icon.

20. The diagnostic instrument according to claim 19, wherein said cholesterol level reading comprises an under 200 (mg/dl) reading, a 200 to 240 (mg/dl) reading and an over 240 (mg/dl) reading.

21. The diagnostic instrument according to claim 20, wherein said second control circuit causes said liquid crystal display to exhibit prompt icons during usage of said instrument, said icons comprising an add blood icon, a timer icon, and an error icon.

22. The diagnostic instrument according to claim 21, wherein said second control circuit causes said liquid crystal display to exhibit a cholesterol level reading, said cholesterol level reading comprising an under 200 (mg/dl) reading, a 200 to 240 (mg/dl) reading, and an over 240 (mg/dl) reading.

23. The diagnostic instrument according to claim 22, wherein said keying guides include at least one lateral edge guide for engaging a lateral edge of said strip, and an angled fore guide for engaging an angled fore edge of said strip, said angled fore guide being positioned off-center with respect to said strip, such that said angled fore edge of said strip can properly engage said angled fore guide only when said strip is properly positioned in said instrument housing.

24. The instrument according to claim 23, wherein a sensor switch is located adjacent said fore guide for activating said first control circuit in response to said strip being placed in said instrument.

25. The diagnostic instrument according to claim 24, wherein said display comprises a liquid crystal display.

26. The diagnostic instrument according to claim 25, wherein said light source comprises a light emitting diode, and said photodetector comprises a silicon photodiode.

27. The diagnostic instrument according to claim 26, wherein said test area comprises a planar surface, said light emitting diode is mounted with its longitudinal light emitting axis substantially perpendicular to said planar surface, and said photodiode is mounted spaced from said light emitting diode with its longitudinal light detecting axis substantially perpendicular to said planar surface.

28. The diagnostic instrument according to claim 27, wherein a flare screen extending substantially perpendicular to said planar surface is positioned between said light emitting diode and said photodetector.

29. The diagnostic instrument according to claim 28, wherein an optical filter, having bandpass wavelengths matching said desired wavelengths, is mounted over said light emitting diode and said phototdetector.

30. An electronic instrument for use with a chemical test strip with a simplified user interface comprising:

a. an instrument having keying guides defining a location at which a chemical test strip is placed;

b. a sensor switch located adjacent to said keying guides for activating said instrument in response to said strip being inserted into said instrument, wherein said insertion activates said instrument; and means is provided for testing the performance of said instrument comprising:

c. A control circuit, the switch connected to the control circuit for activation of the instrument by providing power to the instrument in order to operate the instrument;

d. a first strip having a defined reflectance, said strip engaging said sensor switch to activate a first control circuit to measure reflectance of said first strip when inserted into said instrument; and e. a second strip, insertable into said instrument after removal of said first strip wherein the edges of said second strip do not engage said sensor switch when said second strip is inserted into said instrument, and further comprising two regions of defined reflectance, wherein said first region is used as an indicator to said first control circuit that said strip is being measured, and said second region defining the change in measured reflectance;

wherein said instrument measures the change in reflectance of said strip in response to a test solution being applied to said strip, and wherein said keying guides include at least one lateral edge guide for engaging a lateral edge of strip and an angled fore guide for engaging an angled fore edge of said strip.

31. The electronic instrument according to claim 30 wherein said first and second strips comprise the top side and bottom side of a single strip.

* * * * *

UNITED STATES PATENT AND TRADEMARK OFFICE
CERTIFICATE OF CORRECTION

PATENT NO. : 5,795,543
DATED : August 18, 1998
INVENTOR(S) : Edward M. Poto; Kenneth R. Strahs; Timothy J. Conner; Francis T. Delahanty; Michael Moorman; and Henry Wieck It is certified that error appears in the above-indentified patent and that said Letters Patent is hereby corrected as shown below:

On the title page, item [*] Notice: Pat. No. 5,728,358 should be --Pat. No. 5,728,352.--

Signed and Sealed this

Fifteenth Day of December, 1998

*Attest:*

BRUCE LEHMAN

*Attesting Officer*     *Commissioner of Patents and Trademarks*